Figure 1:
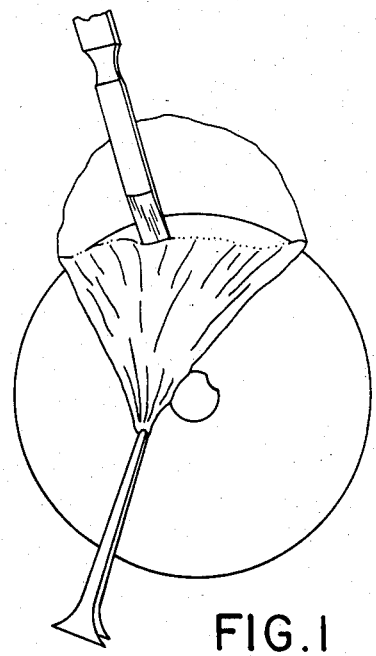

United States Patent [19]

Choyce

[11] Patent Number: 4,607,617
[45] Date of Patent: Aug. 26, 1986

[54] APPARATUS AND METHOD FOR IMPROVING EYESIGHT

[76] Inventor: David P. Choyce, 9 Drake Road, Westcliff on Sea, England

[21] Appl. No.: 419,902

[22] Filed: Sep. 20, 1982

Related U.S. Application Data

[63] Continuation-in-part of Ser. No. 287,628, Jul. 28, 1981, abandoned.

[30] Foreign Application Priority Data

Aug. 5, 1980 [GB] United Kingdom ................. 8025426
May 11, 1981 [GB] United Kingdom ................. 8114325

[51] Int. Cl.⁴ ..................... A61B 19/00; A61F 17/32; A61F 2/14
[52] U.S. Cl. .................................. 128/1 R; 128/305; 623/5
[58] Field of Search ................ 3/13, 1; 128/305, 1 R, 128/303 R; 623/4-6

[56] References Cited

U.S. PATENT DOCUMENTS

| 2,714,721 | 8/1955 | Stone | 3/13 |
| 3,910,296 | 10/1975 | Karageozian et al. | 3/13 X |
| 3,928,294 | 12/1975 | Crawford et al. | 3/1 X |
| 4,092,743 | 6/1978 | Kelman | 3/13 |
| 4,163,609 | 8/1979 | Neefe | 351/160 H |
| 4,257,521 | 3/1981 | Poler | 3/13 X |
| 4,285,073 | 8/1981 | Szycher | 3/13 |

FOREIGN PATENT DOCUMENTS

| 2607462 | 9/1977 | Fed. Rep. of Germany . |
| 2046099 | 3/1980 | United Kingdom . |
| 388746 | 10/1973 | U.S.S.R. ................. 3/13 |

OTHER PUBLICATIONS

Corneal Surgery, Advanced Techniques in Ophthalmic Microsurgery (Book) by Louis J. Girard, vol. two, The C. V. Mosby Co., 1981, pp. 143-149, 168-170.
Concise Guide to Biomedical Polymers (Book) by John W. Boretos, Charles C. Thomas publisher, 1973, pp. 143-144.
Lytle et al., "Wideband Optical Transmission Properties of Seven Thermoplastics", Applied Optics, vol. 18, No. 11, Jun 1, 1979.

Primary Examiner—Ronald L. Frinks
Attorney, Agent, or Firm—Hugh D. Jaeger

[57] ABSTRACT

The invention relates to an implant made of a polysulfone plastics material and designed to be implanted between the layers of the cornea to correct eyesight defects. The implant can as act as a substitute for conventional spectacles and can additionally strengthen and shape the cornea to assist in treating corneal astigmatism and conical cornea.

7 Claims, 11 Drawing Figures

APPARATUS AND METHOD FOR IMPROVING EYESIGHT

The present invention is a continuation in part of U.S. application Ser. No. 287,628 filed by me on July 28th 1981 now abandoned.

The invention relates to an implant to be surgically inserted in an eye in order to correct for defects in eyesight. The invention also relates to a method of treatment for improving eyesight.

There have already been proposed artificial lenses for implantation in a human eye. Such implants have hitherto been intended not as corrective lenses but as substitutes for the natural lens in the eye. When an eye develops a cataract, the natural lens becomes fogged or opaque thereby impairing vision and when such a cataract is treated the lens is removed leaving the eye aphakic. It is possible to correct for aphakia using spectacles but because of the degree of correction required the thickness of the spectacles is substantial making them both cumbersome and unattractive.

For this reason, lenses have been designed for correction of aphakia in which the lens is inserted into a part of the eye either during the operation to remove the cataract or as a secondary operation. Such lenses fall into one of three catagories namely anterior chamber implants, posterior chamber implants and iris plane implants, depending on the location of the lens in the eye. Such lenses are of fixed focal length and as the natural lens has been removed the eye is no longer capable of accommodation, that is to say the focal length cannot change to focus at different distances.

It is clear from what has already been said in relation to lenses previously inserted in an eye that these have been remedies adopted as a last resort for treating very serious eye conditions and such lenses could never be prescribed as an alternative to conventional spectacles for a person suffering from only long sight, short sight or astigmatism.

Another form of implant which has been used in the past with some success has been the artificial cornea such as described in U.S. Pat. No. 2,714,721, filed in Jan. 23, 1952, and generally resembling what is known as a kerato-prosthesis. These implants are a replacement for the natural cornea where the cornea has become opaque or fogged as may occur as a result of burns.

Because kerato-prostheses are a replacement for the damaged part of the cornea, after their insertion between the layers of the natural cornea a window is cut out of at least the damaged outer layer to permit the eye to see through the prosthesis which acts as a clear window in place of the natural cornea. If the inner layer of the cornea is undamaged then it is only necessary to trephine the outer layer of the cornea leaving the aqueous humour separated from the surrounding air by the inner layer of the cornea backed by the kerato-prosthesis. Should the inner layer of the cornea also be damaged then it too must be removed leaving the prosthesis as the only layer between the aqueous humour and the ambient air. It will thus be noted that the kerato-prosthesis is always in contact with the air and is held in place by the portions of the natural cornea which remain only around its periphery.

It can once again be seen that such an implant would on no account be considered an alternative to the use of spectacles or contact lenses.

It is known to resort to surgery in order to correct for defects in eyesight. In particular, a surgical technique has been developed (radial keratotomy) in which radial incisions are made in the cornea with the intention that the cornea should heal with a different curvature from its original thereby correcting for the eyesight defect. The number of incisions and their dimensions are varied to allow for different degrees of correction.

Such surgery can never have a fully predictable outcome and furthermore any non-spherical flattening of the cornea on healing results in an eyesight defect which cannot be corrected by the use of spectacles or contact lenses.

It can therefore be seen that despite the known problems and inconvenience caused to wearers of spectacles and contact lenses, no alternative satisfactory proposal has yet been made and it is an object of the present invention to mitigate the foregoing problems.

In accordance with a first aspect of the present invention, there is provided a lens formed of a polysulfone plastics material and adapted to be inserted between the layers of the cornea to correct defects in eyesight.

Because the lens is made of a polysulfone, the lens has a high refractive index relative to that of the cornea, thereby enabling a relatively thin lens to achieve correction of several dioptres. Furthermore, the polysulfone material is relatively permeable to body fluids with the result that the insertion of the lens between the layers of the cornea has been found not to cause damage to the cornea.

It will be noted that this implant differs from that of the earlier mentioned kerato-prosthesis in as much as after its insertion the inlay is entirely embedded in the cornea and it not exposed to the atmosphere nor to the aqueous humour. By contrast, in a kerato-prosthesis, the implant is not surrounded on both sides by layers of cornea and therefore it has not been necessary in such prostheses to provide a flow path for the fluids permeating the layers of the cornea.

A significant advantage can be gained by the use of polysulfone in making of the inlay because the lens can be sterilised prior to insertion by steam autoclaving. This considerably reduces the cost of packaging the implants which need not be packaged in individual sterile containers.

It has been found that bacause of the high refractive index of polysulfones and in particular of Udel (Registered Trade Mark) as sold by the Union Carbide Corporation, it is possible to correct up to +10 dioptres at spectacle distance with a lens of which the maximum thickness is only 0.4 mm and that one can correct −10 dioptres with a differently shaped lens with a thickness of only 0.1 mm at its centre. Despite this small thickness, because of the strength of the polysulfone material, the implant retains sufficient rigidity to enable its insertion by a simple surgical operation which does not involve penetrating the eye with consequent draining of the aqueous humour but only making an incision deep enough to penetrate the outer layer of the cornea to form a pocket for receiving the inlay. The insertion operation is therfore not a major one and because air does not enter the anterior chamber of the eye the post operative recovery time is not prolonged.

Figure 2A:
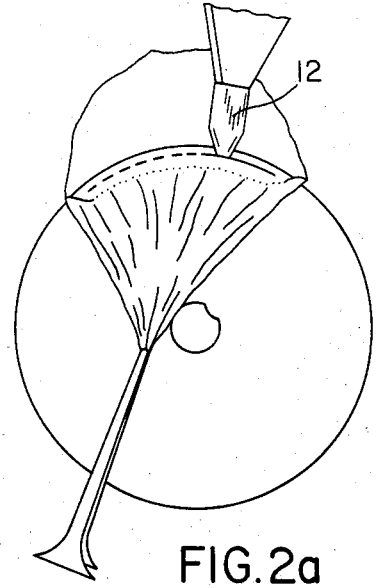
Figure 2B:
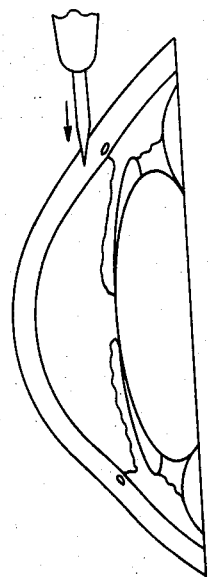
Figure 3B:
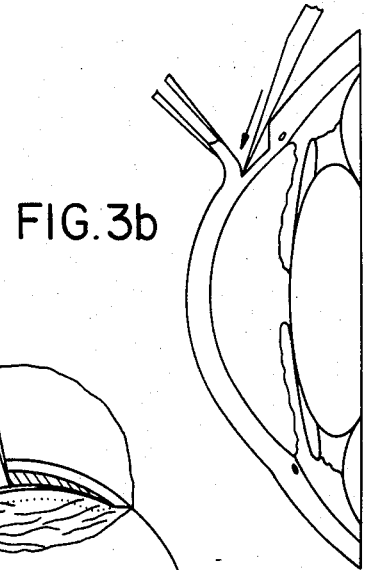
Figure 3A:
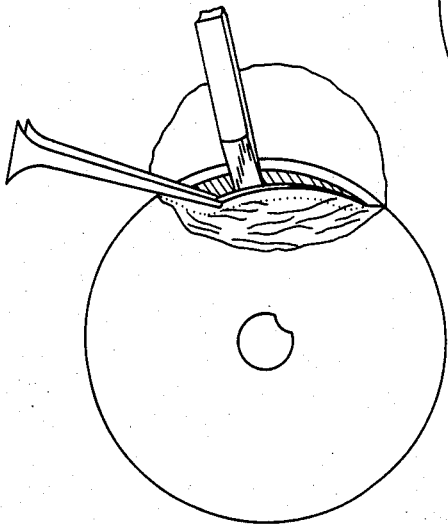
Figure 4A:
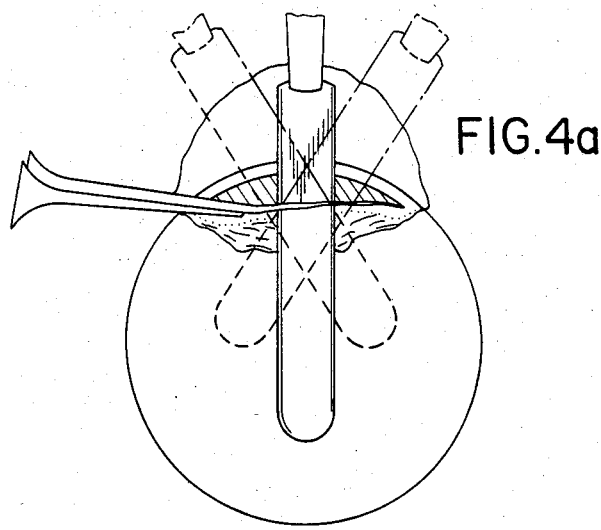
Figure 4B:
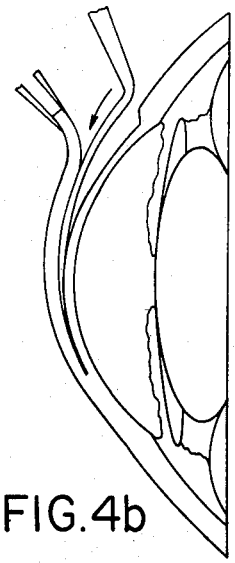
Figure 5:
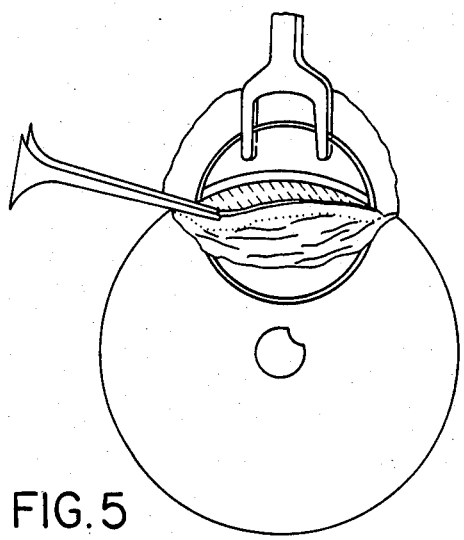
Figure 6:
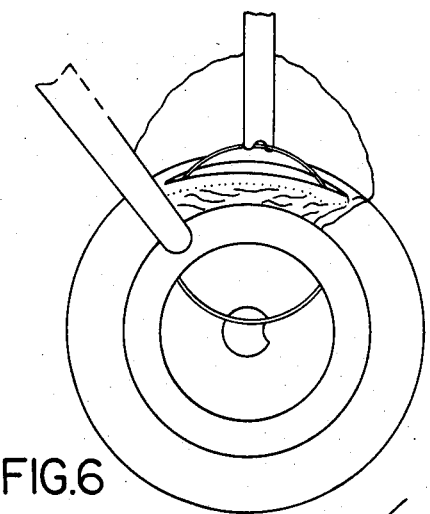
Figure 7A:
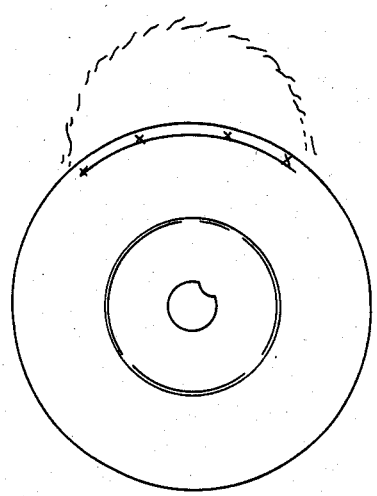
Figure 7B:
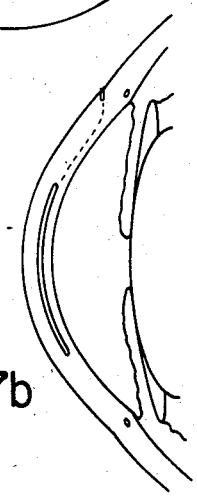

The invention will now be described further, by way of example, with reference to the accompanying drawings, in which:

FIG. 1 shows a front view of the first stage in an operation for inserting an intra-corneal inlay, FIGS. 2a and 2b are a front view and a section, respectively, of the second stage of the operation, FIGS. 3a and 3b are a front view and a sectional view, respectively, showing the third stage of the insertion operation, FIGS. 4a and 4b are a front view and a sectional view, respectively, of a fourth stage of the insertion operation, FIGS. 5 and 6 show front views during a fifth and the sixth stage of the operation, and FIGS. 7a and 7b are a front view and a sectional view, respectively, of the eye after the operation has been completed.

The accompanying drawings illustrate an eye operation for the insertion of an intra-corneal inlay to correct for eyesight defects. The intra-corneal inlay in appearance resembles a conventional contact lens but the radii of curvature of the faces are computed based upon the refractive index relative to the material of the cornea rather than in air. Thus the dimensions will not be the same as a contact lens providing the same degree of correction.

The intra-corneal inlay is made from Udel a material having a high refractive index. The refractive index is typically 1.633 and this is to be compared with 1.49 which is the refractive index of Perspex CQ (Registered Trade Mark). Because of the significant difference in refractive index, it is possible to make the intra-corneal inlay sufficiently thin to be tolerable between the layers of the cornea while still providing the necessary correction. Furthermore, the material can be permeated by the fluid circulating in the cornea, more particularly in view of its small thickness, enabling it to be retained within the cornea without the cornea suffering injury.

In order to correct +10 dioptres (at spectacle distance) a lens made of Udel need only have a maximum thickness of 0.4 mm. To correct −10 dioptres, it is possible to utilise an intra-corneal inlay having a thickness at its centre of only 0.1 mm. More powerful lenses may also be practicable.

The technique of inserting a lens in the cornea also offers the possibility of eliminating regular corneal astigmatism because of the rigidity of the inlay which can strengthen the cornea. The technique of inserting an inlay is furthermore useful in strengthening a congenitally weak cornea as found for example in kerato-conus or conical cornea.

A further advantage stemming from the use of Udel is the ease with which the inlay can be sterilised. This is because the material can withstand high temperatures and is therefore autoclavable. In practice, each corneal inlay is placed carefully in a glass vial containing approximately 3 ml of 0.9% w/v saline solution. Each vial is stoppered and sealed using a crimped aluminum collar. The inlay is then autoclaved in the sealed vial for 40 minutes at 116° C.

In batch processing of inlays, each autoclave batch additionally contains a spore strip packed in an identical vial to the inlay which is analysed after autoclaving. Following autoclaving, each vial in a batch is inspected for integrity of seal and for unwanted inclusions.

The insertion operation will now be described by reference to the drawings. In FIG. 1, a flap of conjunctiva is cut around the periphery of the iris and peeled back to expose the cornea. An incision is made in the upper layer of the cornea using a diamond tipped cutting tool 12. As can be seen from FIG. 2b, the incision is made with the tool lying at an angle of 45° to the surface of the cornea. It is preferable that a guide stop be formed on the cutting tool in order to prevent excessive penetration of the blade into the cornea since is it desirable not to penetrate the inner membrane of the cornea, known as Descemet's membrane.

Once the incision with the sharp diamond tipped blade has been made, a knife with a wider tip is used in a manner shown in FIG. 3 to peel back a small flap from the upper layer of the cornea while still holding the cutting blade at 45° to the surface in the manner shown in FIG. 3b.

After a small flap has been peeled back, it is necessary to form a hollow pocket between the layers of the cornea and this is achieved by inserting a curved instrument with a blunt front end through the incision and the peeled back flap. This is shown in FIGS. 4a and 4b. The instrument is not fully inserted into the cornea but only to a sufficient extent to form a pocket aligned with the pupil of sufficient size to receive the inlay.

Once the pocket has been formed, the inlay is introduced to the pocket using a forked instrument designed for this purpose (see FIG. 5) and subsequently using a fine rod formed with a notch in its end surface the implant is prodded into its desired position. To assist in centering the inlay on the pupil, it is desirable to use an instrument such as shown in FIG. 6 which can readily be positioned in a manner concentric with the pupil. The instrument is merely laid over the eye and serves exclusively to assist in visual alignment. Finally, the flap of cornea is sutured using four stitches as shown in FIG. 7 and the flap of conjuctiva is also folded back and stitched.

I claim:

1. A corneal inlay lens for implant between layers of a cornea of an eye comprising of a polysulfone material of a high refractive index and permeable to body fluids and of a thickness in the range of 0.1 mm to 0.4 mm for insertion between layers of the cornea to correct defects in eyesight.

2. A method of treatment for correcting eyesight defects, which comprises:
   a. forming an incision in the outer layer of the cornea;
   b. separating layers of the cornea to form a pocket;
   c. inserting into the pocket a lens inlay of polysulfone material; and,
   d. resealing the incision.

3. The method of claim 2, comprising the step of peeling a flap of conjunctiva back from around the cornea to expose an edge of the cornea into which edge the incision is made.

4. The method of claim 2 comprising the step of sterilizing the lens by steam autoclaving.

5. The method of claim 2 comprising the step of:
   a. placing the lens in a sealed container containing a saline solution; and,
   b. heating said container to a temperature of 116° C. for 40 minutes.

6. A method of treating an eye suffering from corneal astigmatism which comprises:
   a. implanting between the layers of the cornea an inlay formed of a polysulfone material for strengthening the cornea; and,
   b. constraining the cornea to a spherical configuration.

7. A method of treating an eye suffering from keratoconus which comprises:
   a. implanting between the layers of the cornea an inlay formed of a polysulfone material for strengthening the cornea; and,
   b. constraining the cornea to a spherical configuration.

* * * * *